US005569587A

United States Patent [19]
Waggoner

[11] Patent Number: 5,569,587
[45] Date of Patent: Oct. 29, 1996

[54] METHOD FOR LABELING AND DETECTING MATERIALS EMPLOYING LUMINESCENT ARYSULFONATE CYANINE DYES

[75] Inventor: Alan S. Waggoner, Pittsburgh, Pa.

[73] Assignee: Carnegie Mellon University, Pittsburgh, Pa.

[21] Appl. No.: 424,219

[22] Filed: Apr. 19, 1995

Related U.S. Application Data

[60] Continuation of Ser. No. 882,802, May 14, 1992, abandoned, which is a division of Ser. No. 240,756, Sep. 2, 1988, abandoned, which is a continuation-in-part of Ser. No. 854,347, Apr. 18, 1986, abandoned.

[51] Int. Cl.$^6$ .................................................. C12Q 1/68
[52] U.S. Cl. .............................. 435/6; 436/519; 430/581
[58] Field of Search .................................... 435/6; 436/519, 436/546, 94; 430/581

[56] References Cited

U.S. PATENT DOCUMENTS

| | | | |
|---|---|---|---|
| 3,148,187 | 9/1964 | Heseltine | 260/240.4 |
| 3,423,207 | 1/1969 | Heseltine et al. | 96/84 |
| 3,481,927 | 12/1969 | Heseltine et al. | 260/240.9 |
| 4,040,825 | 8/1977 | Steiger et al. | 430/95 |
| 4,094,745 | 6/1978 | Scholefeld | 435/39 |
| 4,138,551 | 2/1979 | Steiger et al. | 544/212 |
| 4,166,105 | 8/1979 | Hirschfeld | 436/536 |
| 4,256,834 | 3/1981 | Zuk et al. | 435/7.72 |
| 4,268,622 | 4/1981 | Adachi et al. | 430/513 |
| 4,337,063 | 6/1982 | Mihara et al. | 436/536 |
| 4,337,065 | 6/1982 | Hiratsuka et al. | 436/543 |
| 4,343,782 | 8/1982 | Shapiro | 435/7.2 |
| 4,404,289 | 9/1983 | Masuda et al. | 436/538 |
| 4,405,711 | 9/1983 | Masuda et al. | 435/4 |
| 4,414,325 | 11/1983 | Masuda et al. | 435/7.4 |
| 4,429,050 | 1/1984 | Yasuda et al. | 436/538 |
| 4,542,104 | 9/1985 | Stryer et al. | 436/536 |
| 4,584,277 | 4/1986 | Ullman | 435/7.25 |
| 4,748,129 | 5/1988 | Chang et al. | 435/7.25 |
| 4,770,992 | 9/1988 | Van de Engh et al. | 435/6 |
| 4,820,630 | 4/1989 | Taub | 435/5 |
| 4,829,070 | 5/1989 | Bodor | 514/307 |

FOREIGN PATENT DOCUMENTS

| | | |
|---|---|---|
| 669003 | 12/1965 | Belgium. |
| 1529202 | 10/1978 | United Kingdom. |

OTHER PUBLICATIONS

Salama, G., et al. "Sulfhydryl Reagent Dyes Trigger the Rapid Release of $Ca^{2+}$ from Sarcoplasmic Reticulum Vesicles (SR)", Biophysical Journal, vol. 47, 456a (1985).

A. S. Waggoner, et al. "The Kinetics of Conformational Changes in a Region of the Rhodopsin Molecule Away from the Retinylidene Binding Site", Biophysical Journal, vol. 33, 292a (1981).

Jacobson, et al. "International Workshop on the Application of Fluorescence Photobleaching Techniques to Problems in Cell Biology", Federation Proceedings, vol. 42, 72–79 (1973).

L. M. Smith, et al. "The Synthesis of Oligonucleotides containing an aliphotic amino group at the 5' Terminus Synthesis of Fluorescent DNA Primers for use in DNA Sequence Analysis", Nucleic Acids Research, vol. 13, pp. 2399–2407, (1985).

F. W. Hoffman, "Styryl Dyes" Chemical Abstracts: 46–Dyes, vol. 65, Cols. 9070, 9071 and 7072, (1966).

D. M. Sturmer, "Syntheses and Properties of Cyanine and Related Dyes", Special Topics in Heterocyclic Chemistry, vol. 30, Chapter VIII, pp. 441–587 (1977).

F. Hamer, The Cyanine Dyes and Related Compounds, pp. 693, 694 and 704 (1964).

D. M. Sturmer et al., "Sensitizing and Desensitizing Dyes", Special Topics in Heterocyclic Chemistry, Chapter 8, pp. 194–197 (1977).

D. J. Gale et al. "Fibre Reactive Basic Dyes: I–Polymethine Dyes Containing the N–Chloroacetyl Group", J. Soc. Dyers and Colorists, vol. 9, pp. 97–100 (1974).

D. J. Gale et al. "The Amidomethylation and Bromination of Fischer's Base. The Preparation of Some New Polymethine Dyes", Aust. J. Chem., vol. 30, pp. 689–694 (1977).

O. Tadahiro, and U. Nobuhiro, "A New Standard Fluorescence Microsphere for Quantitative Flow Cytometry", Journal of Immunological Methods, vol. 84, pp. 143–154 (1985).

A. N. de Belder, and K. Granath, "Preparation and Properties of Fluorescein–Labelled Dextrans", Carbohydrate Research, vol. 30, pp. 375–378 (1973).

M. Edidin, Y. Zagyansky, T. J. Lardner, "Measurement of Membrane Protein Lateral Diffusion in Single Cells", Science, vol. 191, pp. 466–468 (1976).

R. D. Spencer et al. "Design, Construction, and Two Applications for an Automated Flow–Cell Polarization Fluorometer with Digital Read Out: Enzyme–Inhibitor (Antitrypsin) Assay and Antigen—Antibody (Insulin–Insulin Antiserum) Assay", Clinical Chem. vol. 19, No. 8, pp. 838–844 (1973).

M. J. Anderson, and M. W. Cohen "Fluorescent Staining of Acetylcholine Receptors in Vertebrate Skeletal Muscle", J. Physiol, vol. 237, pp. 385–400 (1974).

B. S. Packard et al. "Intracellular Dye Heterogeneity Determined by Fluorescence Lifetimes", Biochimica et Biophysica Acta, vol. 769, pp. 201–208 (1984).

P. K. Bhattacharyya et al. "Fluorescent Labelling of Strychnine: A Novel approach for Recognition of Strychnine Binding Sites on Neuronal Membrane", Biochemical and Biophysical Research Communications, vol. 101, No. 1, pp. 273–274 (1981).

(List continued on next page.)

Primary Examiner—W. Gary Jones
Assistant Examiner—Scott Houtteman
Attorney, Agent, or Firm—Kirkpatrick & Lockhart LLP

[57] ABSTRACT

A method for detecting a component of an aqueous liquid comprising adding to the liquid a luminescent dye selected from the group consisting of cyanine, merocyanine and styryl dyes containing at least one sulfonic acid or sulfonate group attached to an aromatic nucleus and reacting the dye with the component. The labeled component is then detected by an optical detection method.

23 Claims, 3 Drawing Sheets

OTHER PUBLICATIONS

H. Haigler et al. "Visualization by Fluorescence of the Binding and Internalization of Epidermal Growth Factor in Human Carcinoma Cells A–431", Proc. Natl. Acad. Sci. USA, vol. 75, No. 7, pp. 3317–3321 (1978).

C. B. Neblette, Fundamentals of Photography, pp. 41–42 (undated).

B. C. F. Chu et al., "Derivation of Unprotected Polynucleotides", Nucleic Acids Research, vol. 11, No. 18, pp. 6513–6529 (1983).

H. Hayatsu, "Reaction of Cytidine with Semicarbazide in the Presence of Bisulfite. A Rapid Modification Specific for Single–Stranded Polynucleotide", Biochemistry, vol. 15, No. 12, pp. 2677–2682 (1976).

K. Venkataraman, The Chemistry of Synthetic Dyes, vol. IV, pp. 212–213 (1971).

P. Brandtzaeq, "Rhodamine Conjugates: Specific and Nonspecific Binding Properties in Immunohistochemistry", Annals N.Y. Acad. of Science, vol. 254, pp. 35–55 (1975).

M. R. Loken et al., "Lymphoid Cell Analysis and Sorting", Flow cytometry and Sorting, pp. 505, 522–523, (1979).

R. M. McKinney et al. "An Approach to Quantitation in Rhodamine Isothiocyanate Labeling", Annals N.Y. Acad. of Sciences, vol. 254, pp. 55–65 (1975).

G. E. Ficken, "Cyanine Dyes", Chapter V (undated).

M. N. Kronick and Paul Grossman, "Immunoassay Techniques with Fluorescent Phycobiliprotein Conjugates", Reprinted from Clinical Chemistry, vol. 29, pp. 1582–1586 (1983).

A. N. Glazer and L. Stryer, "Phycofluor Probes" Emerging Techniques, TIBS, pp. 423–427 (1984).

R. T. Morrison et al. "Preparation of Sulfonic Acids", Organic Chemistry, 2nd Edition, pp. 701–704 (Oct. 1969).

K. A. Muirhead et al. "Flow Cytometry: Present and Future" Review, Biotechnology, vol. 3 (Apr. 1985).

J. S. Ploem "General Introduction" Fifth International Conference on Immunofluorescence and Related Staining Techniques, Annals of the N.Y. Academy of Sciences, vol. 254, pp. 1–20 (1975).

R. P. Haugland, "Covalent Fluorescent Probes" Excited States of Biopolymers, Plenum Press pp. 29–58 (undated).

F. Hamer, Cyanine Dyes and Related Compounds, Interscience Publishers, pp. 86–350, 398–399, 460–463, 482–495 and 511–513, (1964).

L. Stryer, "Fluorescent Conjugates for Analysis of Molecules and Cells" Biochem. Methods, vol. 59, paragraph 99:154827f p. 311 (1984).

Bayer et al., Proc. Nat'l Head Sci., USA, vol. 78, No. 9, Sep. 1981, pp. 5618–5622.

Biosis Abstract No. 78081829, Latt et al., Cytometry 5(4), 1984 pp. 339–347.

METHOD FOR LABELING AND DETECTING MATERIALS EMPLOYING LUMINESCENT ARYSULFONATE CYANINE DYES

This invention was made in part under National Institutes of Health contract numbers NIH-NS-19353 and NIH-GM-34639.

This application is a continuation of Ser. No. 07/882,802, filed May 14, 1992 which is a divisional of Ser. No. 07/240,756, filed Sep. 2, 1988 which is a continuation-in-part of Ser. No. 06/854,347, filed Apr. 18, 1986, all abandoned.

BACKGROUND OF THE INVENTION

Cyanine and related polymethine dyes having light absorbing properties have been employed in photographic films. Although such dyes require light absorbing properties, they do not require luminescence (fluorescence or phosphorescence) properties. Cyanine dyes having luminescence properties heretofore have had very limited utilization. One such utilization involved specifically labeling the sulfhydryl group of proteins. In one report, Salama, G., Waggoner, A. S., and Abramson, J., have reported under the title Sulfhydryl Reagent Dyes Trigger the Rapid Release of $Ca^{2+}$ from Sarcoplasmic Reticulum Vesicles (SR), *Biophysical Journal*, 47, 456a (1985) that cyanine chromophores having an iodoacetyl group was used to form covalent bonds with sulfhydryl groups on the Sarcoplasmic Reticulum protein at pH 6.7 to trigger $Ca^{2+}$ release. The report also stated that fluorescent dyes were used to label and isolate those proteins.

In a report of Waggoner, A. S., Jenkins, P. L., Carpenter, J. P., and Gupta, R., entitled the Kinetics of Conformational Changes in a Region of the Rhodopsin Molecule Away From the Retinylidene Binding Site, *Biophysical Journal*, 33, 292a (1981) the authors state that the sulfhydryl group on the F1 region of cattle rhodopsin has been covalently labeled with a cyanine dye having absorbance at 660 nm. Again, this report used cyanine dyes for labeling specifically the sulfhydryl group of a protein, but does not disclose that fluorescent dyes were used.

An article entitled International Workshop on the Application of Fluorescence photobleaching Techniques to Problems in Cell Biology, Jacobson K., Elson E., Koppel D., Webb W., Fed. Proc. 42:72–79 (1983), reports on a paper delivered by A. Waggoner relating to cyanine-type fluorescent probes which can be conjugated to proteins and can be excited in the deeper red region of the spectrum.

The only cyanine probes mentioned in any of the above three reports are those which covalently attach specifically to the sulfhydryl group of a protein. The only specific cyanine compound mentioned is one having an iodoacetyl group, which group causes the cyanine dye to be covalently reactive with a sulfhydryl group. None of the articles listed above discloses the covalent reaction of a cyanine dye with any material other than a protein or with any group on a protein other than a sulfhydryl group.

However, many non-protein materials do not have sulfhydryl groups and many proteins do not have a sufficient number of sulfhydryl groups to make these groups useful for purposes of fluorescence probing. Furthermore, sulfhydryl groups (—SHSH—) are easily oxidized to disulfides (—S—S—) in the presence of air and thereby become unavailable for covalent attachment to a fluorescence probe.

SUMMARY OF THE INVENTION

In accordance with the present invention, cyanine and related polymethine dyes have been developed having substitutent groups which are covalently reactive under suitable reaction conditions not only with sulfhydryl groups but also with amine (—$NH_2$) and hydroxy (—OH) groups or other groups such as aldehyde (—CHO) groups on proteins and other materials for purposes of fluorescence and phosphorescence detection of those materials. The present invention offers considerable advantages over the use of the iodoacetyl cyanine dye of the prior art and its specific reactivity with sulfhydryl groups. Amine and hydroxy groups are more prevalent in proteins and other materials than are sulfhydryl groups and are more stable. Thereby, when fluorescent cyanine dyes are used for detecting the presence of certain proteins, a stronger fluorescent or phosphorescent light intensity signal will be given off because a larger number of dye molecules can be attached to the protein which is being probed. Furthermore, amine and hydroxy groups are more easily added to components which it is desired to label, such as polymer particles, which do not naturally contain either sulfhydryl, amine or hydroxy groups.

This invention also relates to a method wherein luminescent cyanine dyes which contain a group which is covalently reactive with amine or hydroxy or other reacting groups are used to label proteins or other materials having an amine or hydroxy group or other group capable of reacting with the dye in a mixture so that the presence and amount of labeled protein or other material can be detected after the labeled components have been separated by chromatographic methods. According to the above cited references, apparently the sulfhydryl group was selected for covalent reaction specifically because there are so few of these groups on a protein molecule and because in some cases the sulfhydryl group plays a significant role in the function of the protein. Therefore, it was possible for the authors to attempt to ascertain the specific location of a sulfhydryl group on a protein structure. Also, in those references the sulfhydryl-specific dye was used as a probe to detect 6r to produce structural changes in a specific protein. Then, in order to interpret a change in light absorption by the dye or the calcium ion released by dye binding, it was necessary to know where the probe is bound.

Because there are so few sulfhydryl groups on most protein molecules, those groups may not be sufficiently numerous to provide adequate total luminescence for detection studies. In contrast, amine and hydroxy groups are significantly more numerous and are widely dispersed on a protein molecule enabling a fluorescent probe to be attached to multiple sites on the molecule, thereby precluding interpretation of light absorption or fluorescence changes, by facilitating the detection of the protein.

The present invention relates to the labeling with luminescent polymethine cyanine and related polymethine dyes, such as merocyanine and styryl, of proteins and other materials, including nucleic acids, DNA, drugs, toxins, blood cells, microbial materials, particles, plastic or glass surfaces, polymer membranes, etc., at an amine or hydroxy site on those materials. The dyes are advantageously soluble in aqueous or other medium in which the labeled material is contained. The present invention relates to a two-step labeling process in addition to a single step labeling process. In the two-step labeling process, a primary component, such as an antibody, can be labeled at sites thereon, including amine, hydroxy, aldehyde or sulfhydryl sites, and the labeled component is used as the probe for a secondary component, such as an antigen for which the antibody is specific.

In the prior art discussed above, specificity of site of attachment by a cyanine probe was achieved by using a probe which is covalently reactive with a sulfhydryl group. According to the two-step method of the present invention, cyanine and related probes can be reacted in a first step with an amine, aldehyde, sulfhydryl, hydroxy or other groups on a first component, such as an antibody, and then the antibody can achieve the desired specificity in a second component, such as an antigen, in a second or staining step, the specificity being determined by the antigen site of attachment to the antibody.

The present invention is directed also to the luminescent polymethine cyanine and related compounds which contain groups enabling them to be covalently attached to amine, hydroxy, aldehyde or sulfhydryl groups on a target molecule. It is directed to monoclonal antibodies and other components labeled with these luminescent cyanine compounds which are capable of being probes for antigens. When the target is a type of cell, the present invention can be employed to measure the amount of labeled antibodies which are attached to that type of cell. The measurement can be made by determining the relative brightness or dimness of the luminescence of the cells.

The present invention can be employed to determine the concentration of a particular protein or other component in a system. If the number of reactive groups on a protein which can react with a probe is known, the fluorescence per molecule can be known and the concentration of these molecules in the system can be determined by the total luminescence intensity of the system.

The method can be employed to quantify a variety of proteins or other materials in a system by labeling all of a mixture of proteins in the system and then separating the labeled proteins by any means, such as chromatographic means. The amount of separated proteins that are luminescent can then be determined. In chromatographic detection systems, the location of the dye on the labeled material can be ascertained.

This invention can also be employed to determine the number of different cells which are tagged by an antibody. This determination can be made by tagging a plurality of types of cells in a system, and then separating the tagged cells outside of the system. Also, tagged cells can be separated from nontagged cells outside of the system.

Another embodiment of the present invention comprises a multiparameter method employing a plurality of luminescent cyanine or related dyes attached respectively to a plurality of different primary components, such as antibodies, each specific for a different secondary component, such as an antigen, in order to identify each of a plurality of said antigens in a mixture of antigens. According to this embodiment, each of said antibodies is separately labeled with a dye having a different light absorption and luminescence wavelength characteristics than the dye used for labeling the other probes. Then, the labeled antibodies are all added to a biological preparation being analyzed containing secondary components, such as antigens, which can be respectively stained by particular labeled antibodies. Any unreacted dye materials may be removed from the preparation as by washing, if they interfere with the analysis. The biological preparation is then subjected to a variety of excitation wavelengths, each excitation wavelength used being the excitation wavelength of a particular conjugated dye. A luminescence microscope or other luminescence detection system, such as a flow cytometer or fluorescence spectrophotometer, having filters or monochrometers to select the rays of the excitation wavelength and to select the wavelengths of luminescense is employed to determine the intensity of rays of the emission wavelength corresponding to the excitation wavelength. The intensity of luminescence at wavelengths corresponding to the emission wavelength of a particular conjugated dye indicates the quantity of antigen which has been bound to the antibody to which the dye is attached. In certain cases as single wavelength of excitation can be used to excite luminescence from two or more materials in a mixture where each fluoresces at a different wavelength and the quantity of each labeled species can be measured by detecting its individual fluorescence intensity at its respective fluorescence wavelength. If desired, a light absorption detection method can be employed. The two-step method of the invention can be applied to any system in which a primary material conjugated with a dye is used in a luminescence or light absorption detection system to detect the presence of another material to which the primary material-dye conjugate is directed. For example, the dye can be conjugated to a fragment of DNA or RNA to form a dye conjugated DNA or RNA fragment which is then directed to a main strand of DNA or RNA to which the piece is complementary. The same test method can be employed to detect the presence of any complementary main strand of DNA.

The cyanine and related dyes of this invention are especially well adapted for the analysis of a mixture of components wherein dyes of a variety of excitation and emission wavelengths are required because specific cyanine and related dyes can be synthesized having a wide range of excitation and emission wavelengths. Specific cyanine and related dyes having specific excitation and emission wavelengths can be synthesized by varying the number of methine groups or by modifying the cyanine ring structures. In this manner, it is possible to synthesize dyes having particular excitation wavelengths to correspond to a particular excitation light source, such as a laser, e.g., a HeNe laser or a diode laser.

This invention relates to the covalent reaction of highly luminescent and highly light absorbing cyanine and related dye molecules under reaction conditions to amine, hydroxy, aldehyde, sulfhydryl or other groups on proteins, peptides, carbohydrates, nucleic acids, derivatized nucleic acids, lipids, certain other biological molecules, biological cells, as well as to non-biological materials, such as soluble polymers, polymeric particles, polymer surfaces, polymer membranes, glass surfaces and other particles and surfaces. Because luminescence involves highly sensitive optical techniques, the presence of these dye "labels" can be detected and quantified even when the label is present in very low amounts. Thus the dye labeling reagents can be used to measure the quantity of a material that has been labeled. The most useful dyes are highly light absorbing ($\epsilon$=70,000 to 250,000 liters per mole centimeter, or higher) and very luminescent and they have quantum yields of at least 5% to 86%, or more. The qualities apply to the dyes themselves and to the dyes conjugated to a labeled material.

An important application for these color labeling reagents is the production of luminescent monoclonal antibodies. Monoclonal antibodies are protein molecules that bind very tightly and very specifically to certain chemical sites or "markers" on cell surfaces or within cells. These antibodies, therefore, have an enormous research and clinical use for identifying certain cell types (e.g. HLA classification, T-cell subsets, bacterial and viral classification, etc.) and diseased cells. In the past, the amount of antibody bound to a cell has been quantified by tagging the antibody in various ways.

Tagging has been accomplished with a radioactive label (radio immunoassay), an enzyme (ELISA techniques), or a fluorescent dye (usually fluorescein, rhodamine, Texas Red® or phycoerythrin). Most manufacturers and users of clinical antibody reagents would like to get away from the problems involved in the use of radioactive tracers so luminescence is considered one of the most promising alternatives. In fact, many companies now market fluorescein, Texas Red®, rhodamine and phycoerythrin labeled monoclonal antibodies.

In recent years, optical/electronic instrumentation for detecting fluorescent antibodies on cells has become more sophisticated. For example, flow cytometry can be used to measure the amount of fluorescent antibody on individual cells at a rate up to 5,000 cells per second. Microscopy and solution fluorescence techniques have also advanced. These instruments can excite fluorescence at many wavelengths of the UV, visible, and near IR regions of the spectrum. Yet most of the useful fluorescent labeling reagents available today can be excited only in the 400–580 nm region of the spectrum. The exceptions are some of the phycobiliprotein-type pigments isolated from marine organisms which can be covalently attached to proteins and which can be excited at somewhat longer wavelengths. Therefore, there is a large spectral window ranging from 580 to roughly 900 nm where new labeling reagents need to become available for labeling biological and non-biological materials for analysis with now available instrumentation. New reagents excitable in this spectral region would make it possible to perform multicolor luminescence analyses of markers on cells because antibodies with different specificites could each be tagged with a different colored fluorescent dye. Thus the presence of several markers could be determined simultaneously for each cell analyzed.

This invention also relates to the luminescent (fluorescent or phosphorescent) cyanine, merocyanine and styryl dyes themselves that can be covalently linked to biological and non-biological materials. Merocyanine and styryl dyes are considered to be related to cyanine dyes for purposes of this invention. The new labeling reagents themselves, but more particularly when conjugated to a labeled component, can be excited by light of first defined wavelengths, e.g. by light in wavelength regions of the spectrum ranging from 450 nm to 900 nm. Background fluorescence of cells generally occurs at a lower wavelength. Therefore, the labeling reagents will distinguish over background fluorescence. Particularly of interest are the derivatives that absorb light at 633 nm since they can be excited by inexpensive, intense, stable, long-life, HeNe laser sources. Light of second defined wavelengths that is fluoresced or phosphoresced by the labeled component can then be detected. The fluoresced or phosphoresced light generally has a greater wavelength than the excitation light. The detection step can employ a luminescence microscope having a filter for absorption of scattered light of the excitation wavelength and for passing the wavelength that corresponds to the luminescence corresponding to the particular dye label used with the specimen. Such an optical microscope is described in Ser. No. 711,065, filed Mar. 12, 1985.

Not all cyanine and related dyes are luminescent. However, the dyes of this invention include those of the cyanine and related dyes which are luminescent. They are relatively photostable and many are soluble in the reaction solution, preferably a water solution. The conjugated dyes themselves, but more particularly when conjugated to a labeled component, have molar extinction coefficients ($\epsilon$) of at least 50,000, and preferably at least 100,000 liters per mole centimeter. The extinction coefficient is a measure of the capability of the molecules to absorb light. The conjugated dyes of this invention have quantum yields of at least 2 percent and preferably at least 10 percent. In addition, the conjugated dyes of this invention absorb and emit light in the 400 to 900 nm spectral range, and preferably in the 600 to 900 nm spectral range.

ARYLSULFONATED DYES

It has now been found that arylsulfonate or arylsulfonic acid substituted dyes as described herein are intrinsically more fluorescent and have improved photostability and water solubility as compared to similar dyes without an arylsulfonate or arylsulfonic acid group. The term arylsulfonate or arylsulfonic acid as used herein and in the claims refers to arylsulfonic acid groups or arysulfonate groups, interchangeably, wherein said groups are attached to an aromatic ring structure, including a single ring aromatic structure or a fused ring structure, such as a naphthalene structure. The single ring aromatic structure or fused ring aromatic structure can be present in polymethine cyanine, merocyanine or styryl type dyes.

Many dyes with planar molecular structures, including ordinary cyanine dyes, tend to form dimers and higher order aggregates in aqueous solution, particularly when inorganic salts are also present, as in buffered solutions and physiological salines. These aggregates usually have absorption bands shifted to the short wavelength side of the monomer absorption and are generally very weakly fluorescent species. The tendency of cyanine dyes to readily form aggregates in aqueous solution is well known, particularly in the photographic industry (West, W., and Pierce, S., *J. Phys. Chem.*, 69:1894(1965); Sturmer, D. M., *Spec. Top in Heterocyclic Chemistry*, 30 (1974)).

Many dye molecules, and particularly cyanine dye molecules, tend to form aggregates in aqueous solution. It has been found that the arylsulfonate dyes have a minimal tendency to form these aggregates. The arylsulfonate dyes when used to form fluorescent labeling reagents will have a reduced tendency to form aggregates when they are bound at high surface densities to protein or other molecules such as antibodies. The tendency of a particular dye molecule to form aggregates in a salt solution (e.g. 150 mM sodium chloride) can be taken as a measure of the tendency of the same dye molecule to form aggregates on the surface of proteins. It is therefore desirable for dye molecules to have a minimal tendency to form aggregates in aqueous salt solutions. The data shown in FIG. 2 can be used to illustrate that a particular arylsulfonated dye, even at high concentrations, has a low tendency to form aggregates in aqueous salt solution.

Figure 1:
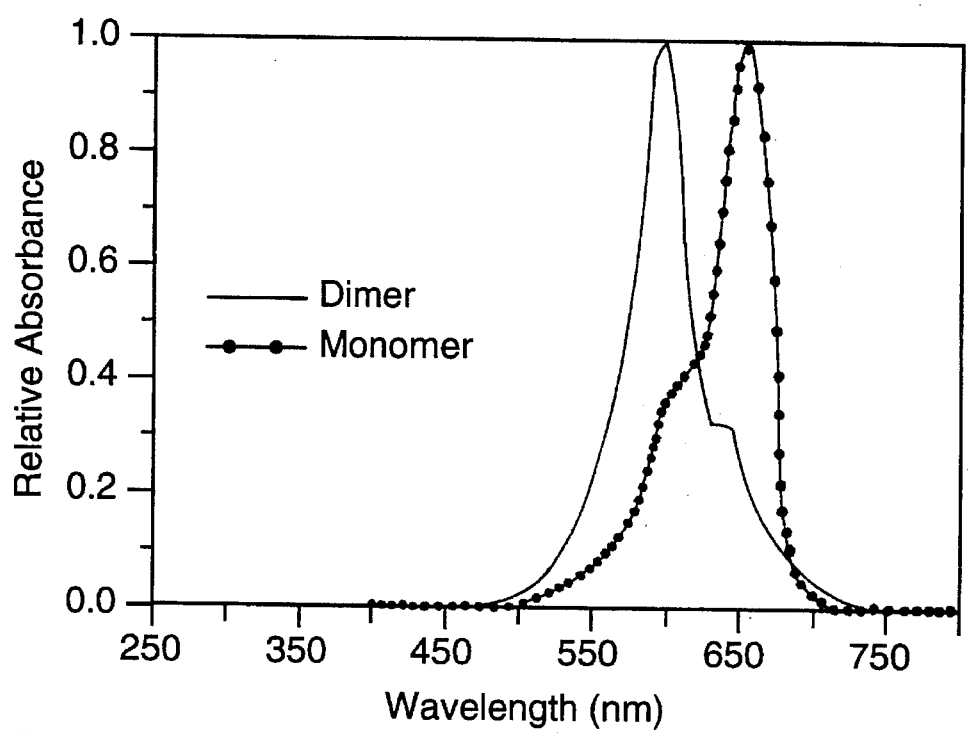
FIG. 1 is a graph showing the monomer absorption spectrum and the dimer absorption spectrum of a typical cyanine dye dissolved in an aqueous buffer.

FIG. 1 shows the monomer absorption spectrum and the dimer absorption spectrum of a typical cyanine dye dissolved in an aqueous buffer. The dye used to generate these spectra, N,N'-di-sulfobutyl-indodicarbocyanine, does not possess arylsulfonate groups and readily forms dimers at concentrations even in the sub millimolar range. The dimer spectrum was calculated from the spectra of the dye at different concentrations (see the method of West and Pearce, 1965). At a concentration of 3 millimolar in phosphate buffered saline solution, the absorbances of the monomer and dimer bands were about equal.

Figure 2:
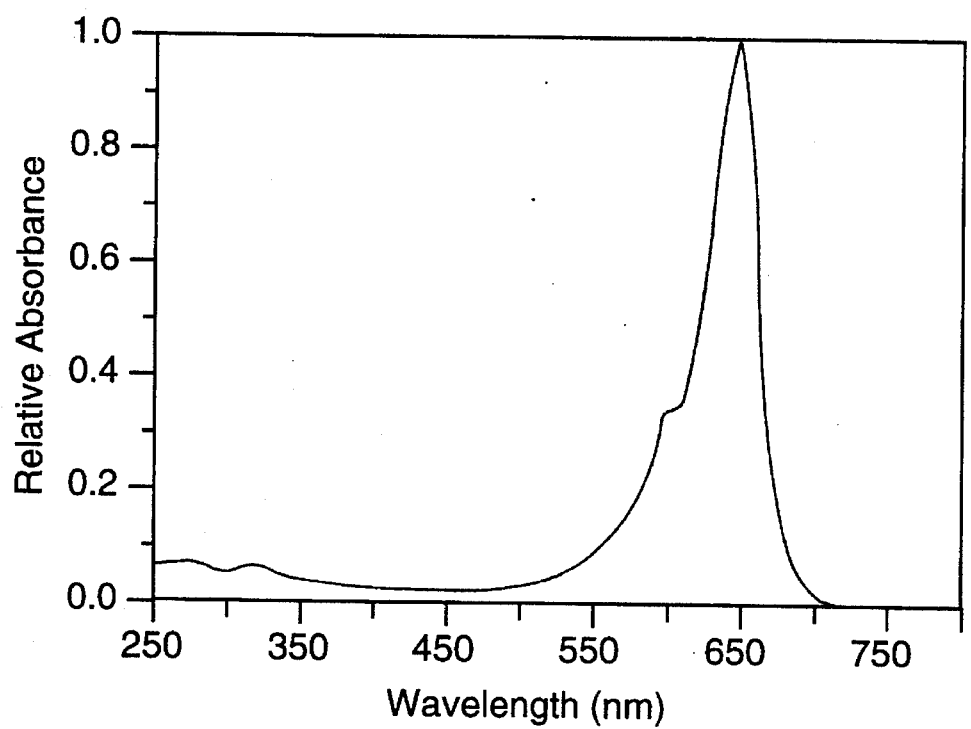
FIG. 2 is a graph showing the absorption spectrum for a particular arylsulfonated dye illustrating that even at high concentrations, the dye has s low tendency to form aggregates in aqueous salt solution.

The spectrum of the improved sulfoindodicarbocyanine, N,N'-diethyl-indodicarbocyanine-5,5'-disulfonic acid, is shown in FIG. 2. This dye showed no evidence of aggregation in the saline solution at concentrations up to 10 millimolar.

Figure 3:
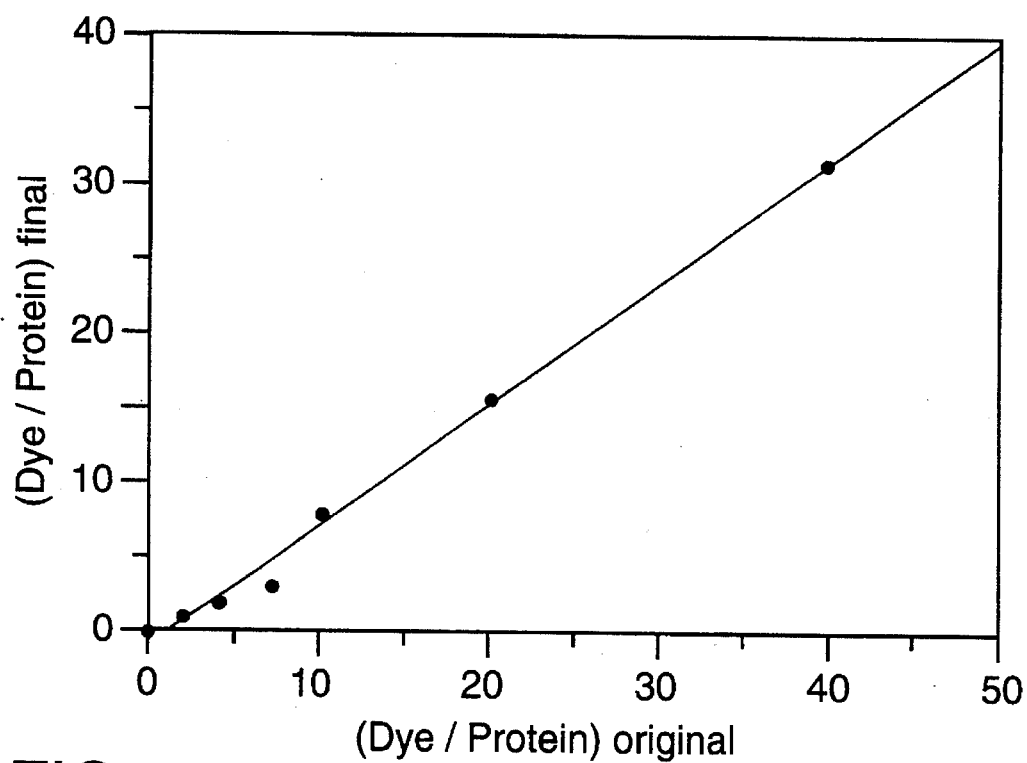
FIG. 3 is a graph showing the molar dye:protein ratio of an active ester of the new sulfoindodicarbocyanine dye.

It is customary to determine the efficiency with which a particular reactive dye couples to a protein, such as an antibody, under defined reaction conditions. The dye tested was the bis-N-hydroxysuccinimide ester of N,N'-di-carboxypentyl-indodicarbocyanine- 5,5'-disulfonic acid. FIG. 3 illustrates that this sulfocyanine dye active ester reacts efficiently with sheep immunoglobulin in a carbonate buffer at pH 9.2 to form covalently labeled antibody molecules that have a dye to antibody mole ratio ranging from less than 1 to more than 20, depending on the relative dye and antibody concentrations in the reaction solution. The slope of the linear least squares fit of the data indicates that under these conditions the labeling efficiency of this dye is about 80%. In similar studies fluorescein isothiocyanate (FITC) reacted with about 20% efficiency.

The reactivity of the active ester of the new sulfoindodicarbocyanine dye was investigated by labeling sheep immunoglobulin (IgG). The protein (4 mg/ml) was dissolved in 0.1 molar carbonate buffer (pH 9.2). Aliquots of the reactive dye dissolved in anhydrous dimethyl formamide were added to the protein samples to give the original dye:protein molar ratios. After thirty minutes the protein was separated from unconjugated dye by gel permeation chromatography (Sephadex G-50). The resulting molar dye:protein ratios Were determined spectrophotometrically and are shown in FIG. 3.

At low dye to protein ratios the absorption spectra of the labeled proteins show bands which correspond closely with the spectra of the free monomeric dye. Antibody molecules which have been heavily labeled (high dye to protein ratios) or which have been labeled with dyes that have a large tendency to aggregate in aqueous solutions are found often to have new absorption peaks which appear at shorter wavelengths than the absorption bands of the monomeric dye in aqueous solution. The wavelength of the new absorption peak frequently falls in a region that is characteristic of the dimer absorption spectrum of the dye (see FIG. 1).

Figure 4:
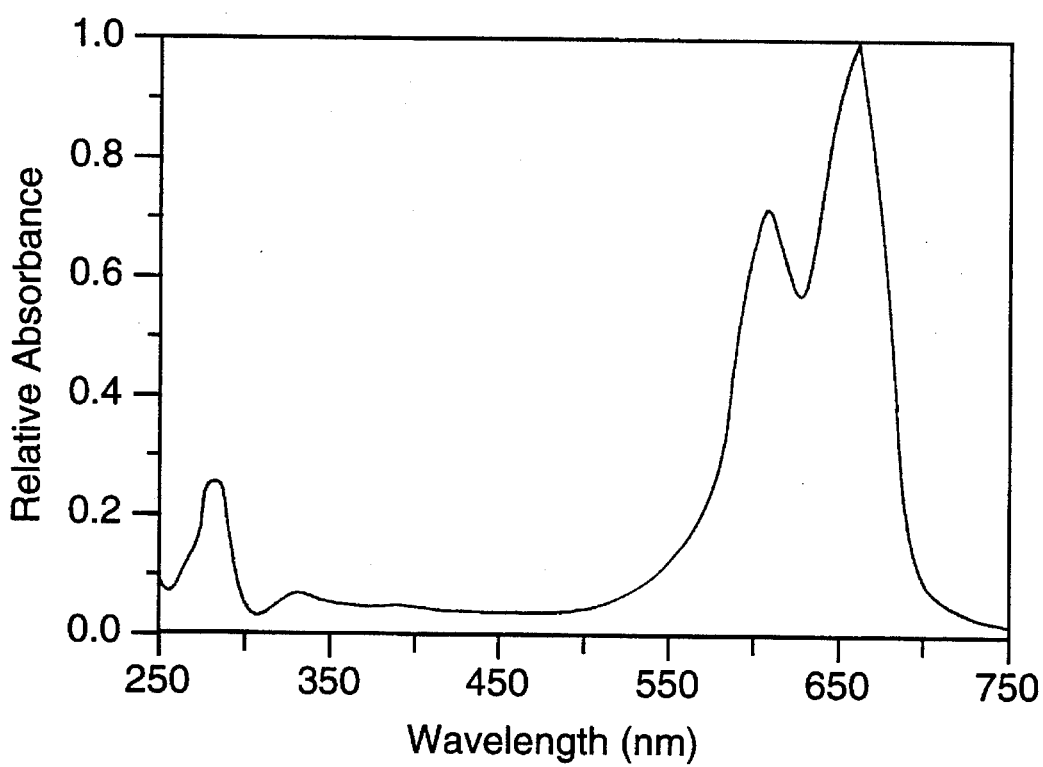
FIG. 4 is a graph showing the antibody absorption spectrum of a labeling reagent which does not possess arylsulfonate groups.

More heavily labeled antibodies have higher ratios of short to long wavelength absorption peaks. This shorter wavelength absorption peak can be seen in FIG. 4 at approximately 590 nm. The longer wavelength peak (at 645 nm) in FIG. 4 is due to monomeric dye molecules bound to the antibody. The labeling reagent used to produce the antibody absorption spectrum in FIG. 4 (the bis-N-hydroxysuccinimide ester of N,N'-di-sulfobytyl-indodicarbocyanine- 5,5'-acetic acid) does not possess arylsulfonate groups and readily forms dimers in aqueous salt solutions and on antibodies with which it has reacted. Of key importance, flourescence excitation spectra of these antibodies show that excitation of the labeled antibodies at the short wavelength peak does not proportionally produce as much fluorescence as does excitation at the longer wavelength peak. This observation is in line with the idea that the shorter wavelength absorption peak is due to the formation of nonfluorescent dimers and aggregates on the antibody molecules.

Figure 5:
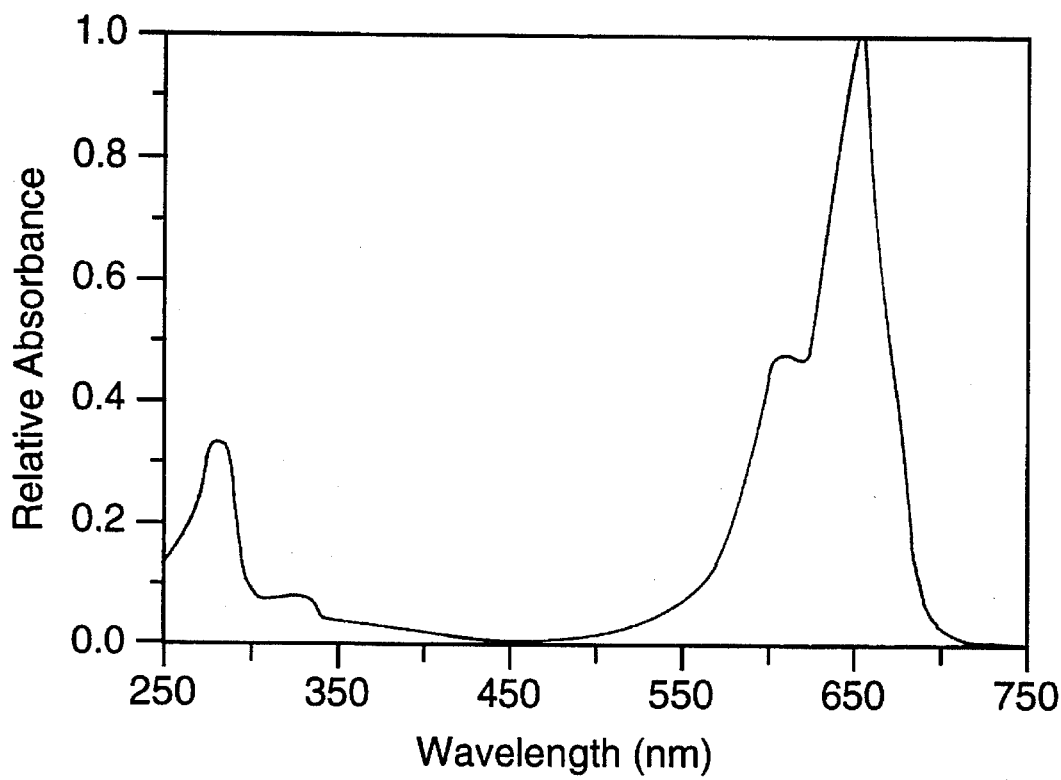
FIG. 5 is a graph showing the antibody absorption spectrum of the arylsulfonate cyanine dye labeling reagent of FIG. 3 showing the much smaller absorption peak at wavelengths where dimers characteristically absorb.

We have found that the aryl sulfonate cyanine dye labeling reagent used in obtaining the data of FIG. 3 does not readily aggregate on the antibody molecules as judged by the much smaller absorption peak at wavelengths where dimers characteristically absorb (see FIG. 5). This is important because antibodies and other proteins labeled with these "non-aggregating" labeling reagents should produce more highly fluorescent labeled proteins. In fact, the arysulfocyanines do produce brightly fluorescent antibodies even when the average dye per antibody ratio is relatively high (see FIG. 6).

Sheep immunoglobulin (IgG) labeled with a carboxyindodicarbocyanine dye is shown in FIG. 4. FIG. 5 shows the protein conjugated with the new sulfoindodicarbocyanine dye. The presence of increased dimer (see FIG. 1) in the former sample is apparent. Although the dye:protein molar ratio was approximately the same in both preparations, the protein represented in FIG. 5 was more fluorescent than the sample shown in FIG. 4.

Figure 6:
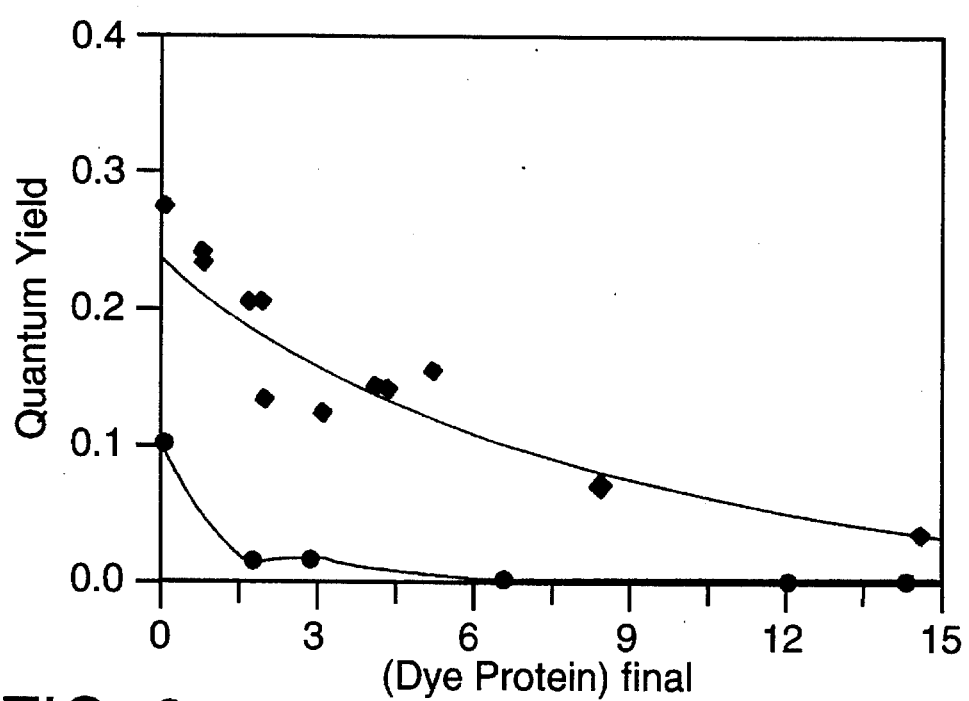
FIG. 6 is a graph comparing the quantum yields of sheep immunoglobulin labeled with the sulfoindodicarbocyanine dye and a protein labeled with an indodicarbocyanine-isothiocyanate reactive dye, showing the change in quantum yield with the change in dye/-protein ratios.

In order to have brightly fluorescing antibodies or other proteins that have been labeled with fluorescent dyes, it is important that the average quantum yield per dye molecule on the protein be as high as possible. It has been generally found that as the surface density of dye molecules on the protein increases (i.e. the dye to protein ratio increases), the average quantum yield of the dyes is reduced. This effect has been sometimes attributed to quenching that occurs as a result of dye-dye interaction on the surface of the more heavily labeled proteins. The formation of nonfluorescent dimers on protein surfaces can certainly contribute to this quenching. FIG. 6 shows that the average quantum yield of an arylsulfocyanine dye decreases slowly as the dye/protein ratio increases (curve with diamond symbols). In contrast, the curve having round symbols shows there is a very rapid decrease in the average quantum yield for the conjugate of a non-arylsulfocyanine dye (N,N'-di-sulfobytyl-indodicarbocyanine- 5-isothiocyanate) as the dye/protein ratio increases. Therefore the sulfocyanine dye illustrated in FIG. 6 produces more brightly fluorescing antibodies than the other dye, especially in the labeling range of 1 to 10 dye molecules per antibody molecule.

The average fluorescence quantum yield of individual dye molecules on labeled proteins is a measure of the fluorescence signal obtainable from these biomolecules. Data from sheep immunoglobulin (IgG) labeled with the new sulfoindodicarbocyanine dye in phosphate buffered saline solution are shown in the curve having diamond symbols of FIG. 6. The curve having round symbols of FIG. 6 shows proteins labeled with an indodicarbocyanine-isothiocyanate reactive dye, for comparison. In FIG. 6, the quantum yields at zero dye/protein ratio represent the values for the methylamine-adducts of the reactive dyes (free dye) in buffer.

BACKGROUND PROCEDURES

Luminescent probes are valuable reagents for the analysis and separation of molecules and cells and for the detection and quantification of other material. A very small number of luminescent molecules can be detected under optimal circumstances. Barak and Webb visualized fewer than 50 fluorescent lipid analogs associated with the LDL reception of cells using a SIT camera, *J. Cell Biol.* 90:595–604 (1981). Flow cytometry can be used to detect fewer than 10,000 fluorescein molecules associated with particles or certain cells (Muirhead, Horan and Poste, *Bio/Technology* 3:337–356 (1985). Some specific examples of application of fluorescent probes are (1) identification and separation of subpopulations of cells in a mixture of cells by the techniques of fluorescence flow cytometry, fluorescence-activated cell sorting and fluorescence microscopy; (2) determination of the concentration of a substance that binds to a second species (e.g., antigen-antibody reactions) in the technique of fluorescence immunoassay; (3) localization of substances in gels and other insoluble supports by the techniques of fluorescence staining. These techniques are described by Herzenberg et al., "Cellular Immunology," 3rd ed., chapt. 22; Blackwell Scientific Publications, 1978 (fluorescence-activated cell sorting); and by Goldman, "Fluorescence Antibody Methods" Academic Press, New York, 1968 (fluorescence microscopy and fluorescence staining); and in Applications of Fluorescence in the Biomedical Sciences, ed. Taylor et al., Alan Liss Inc., 1986.

When employing fluorescers for the above purposes, there are many constraints on the choice of the fluorescer. One constraint is the absorption and emission characteristics of the fluorescer, since many ligands, receptors, and materials in the sample under test, e.g. blood, urine, cerebrospinal fluid, will fluoresce and interfere with an accurate determination of the fluorescence of the fluorescent label. This phenomenon is called autofluorescence or background fluorescence. Another consideration is the ability to conjugate the fluorescer to ligands and receptors and other biological and non-biological materials and the effect of such conjugation on the fluorescer. In many situations, conjugation to another molecule may result in a substantial change in the fluorescent characteristics of the fluorescer and, in some cases, substantially destroy or reduce the quantum efficiency of the fluorescer. It is also possible that conjugation with the fluorescer will inactivate the function of the molecule that is labeled. A third consideration is the quantum efficiency of the fluorescer which should be high for sensitive detection. A fourth consideration is the light absorbing capability, or extinction coefficient, of the fluorescers, which should also be as large as possible. Also of concern is whether the fluorescent molecules will interact with each other when in close proximity, resulting in self-quenching. An additional concern is whether there is nonspecific binding of the fluorescer to other compounds or container walls, either by themselves or in conjunction with the compound to which the fluorescer is conjugated.

The applicability and value of the methods indicated above are closely tied to the availability of suitable fluorescent compounds. In particular, there is a need for fluorescent substances that emit in the longer wavelength visible region (yellow to near infrared), since excitation of these chromophores produces less autofluorescence and also multiple chromophores fluorescing at different wavelengths can be analyzed simultaneously if the full visible and near infrared regions of the spectrum can be utilized. Fluorescein, a widely used fluorescent compound, is a useful emitter in the green region although in certain immunoassays and cell analysis systems background autofluorescence generated by excitation at fluorescein absorption wavelengths limits the detection sensitivity. However, the conventional red fluorescent label rhodamine has proved to be less effective than fluorescein. Texas Red® is a useful labeling reagent that can be excited at 578 nm and fluoresces maximally at 610 nm.

Phycobiliproteins have made an important contribution because of their high extinction coefficient and high quantum yield. These chromophore-containing proteins can be covalently linked to many proteins and are used in fluorescence antibody assays in microscopy and flow cytometry. The phycobiliproteins have the disadvantages that (1) the protein labeling procedure is relatively complex; (2) the protein labeling efficiency is not usually high (typically an average of 0.5 phycobiliprotein molecules per protein); (3) the phycobiliprotein is a natural product and its preparation and purification is complex; (4) the phycobiliproteins are expensive; (5) there are at present no phycobiliproteins available as labeling reagents that fluoresce further to the red region of the spectrum than allophycocyanine, which fluoresces maximally at 680 nm; (6) the phycobiliproteins are relatively chemically unstable; (7) they photobleach relatively easily; (8) the phycobiliproteins are large proteins with molecular weights ranging from 33,000 to 240,000 and are larger than many materials that it is desirable to label, such as metabolites, drugs, hormones, derivatized nucleotides, and many proteins including antibodies. The latter disadvantage is of particular importance because antibodies, avidin, DNA-hybridization probes, hormones, and small molecules labeled with the large phycobiliproteins may not be able to bind to their targets because of steric limitations imposed by the size of the conjugated complex and the rate of binding of conjugates to targets is slow relative to low molecular weight conjugates.

Other techniques involving histology, cytology, immunoassays would also enjoy substantial benefits from the use of a fluorescer with a high quantum efficiency, absorption and emission characteristics at longer wavelengths, having simple means for conjugation and being substantially free of nonspecific interference.

OUTLINE OF INVENTION

This invention employs reactive fluorescent arylsulfonated cyanine and related dyes having relatively large extinction coefficients and high quantum yields for the purpose of detection and quantification of labeled components. Fluorescent cyanine and related dyes can be used to label biological materials such as antibodies, antigens, avidin, streptavidin, proteins, peptides, derivatized nucleotides, carbohydrates, lipids, biological cells, bacteria, viruses, blood cells, tissue cells, hormones, lymphokines, trace biological molecules, toxins and drugs. Fluorescent dyes can also be used to label non-biological materials such as soluble polymers and polymeric and glass particles, drugs, conductor, semiconductor, glass and polymer surfaces, polymer membranes and other solid particles. The component being labeled can be in a mixture including other materials. The mixture, in which the label reaction occurs, can be a liquid mixture, particularly a water mixture. The detection step can occur with the mixture in a liquid or dry condition, such as a microscope slide.

This invention requires cyanine dyes to be modified by the incorporation into the cyanine molecule of a reactive group that will covalently attach to a target molecule, preferably at an amine or hydroxy site, and in some instances at a sulfhydryl or aldehyde site. This invention also employs modification or use of cyanine and related dye structures to enhance their solubility in the test liquid (1) to make their handling easier in labeling reactions, (2) to help prevent aggregation of the dye on the surface of proteins that are being labeled and (3) to help prevent nonspecific binding of labeled materials to biological materials and to surfaces and assay apparatus.

The cyanine and related dyes offer an important advantage over existing fluorescent labeling reagents. First, cyanine and related dyes have been snynthesized that absorb and emit in a region of the spectrum ranging from 400 to nearly 1100 nm. Thus reactive derivatives of these dyes can be made for assays that require simultaneous measurement of a number of labeled materials. Multicolor (or multiparameter) analysis of this sort may be desirable for the sake of simplicity, cost effectiveness, or for determining ratios of different labeled species on each particle in a complex mixture of particles (e.g., ratios of antigen markers on individual blood cells in a complex mixture by multiparameter flow cytometry or fluorescence microscopy). Second, many cyanine and related dyes strongly absorb and fluoresce light. Third, many cyanine and related dyes are relatively photostable and do not rapidly bleach under the fluorescence microscope. Fourth, cyanine and related dye derivatives can be made which are simple and effective coupling reagents. Fifth, many structures and synthetic procedures are available and the class of dyes is versatile. Therefore, many structural modifications can be made to make the reagents more or less water soluble. Their charge can be changed so they will not perturb the molecule to which they are attached and so nonspecific binding can be reduced. Sixth, unlike the phycobiliproteins, the cyanine type dyes are relatively small (molecular weight=1,000) so they don't sterically interfere appreciably with the ability of the labeled molecule to reach its binding sight rapidly or carry out its function.

Thus cyanine type dye labeling agents offer many potential advantages. These dyes can be used to selectively label one or more components in a liquid, especially an aqueous liquid. The labeled components can then be detected by optical or luminescence methods. Alternately, the labeled component can then be used to stain a second component for which it has a strong affinity, and the presence of the second component is then detected by optical or luminescence methods. In this case, the dye is reacted with an amine, hydroxy, aldehyde or sulfhydryl group on the labeled component. For example, the labeled component can be an antibody and the stained component for which it has a strong affinity can be a biological cell, an antigen or a hapten, or a biological cell or particle containing said antigen or hapten. In another example, the label component is avidin and the stained component can be biotinylated materials. Also, lectins conjugated with polymethine cyanine type dyes can be used to detect and quantify specific carbohydrate groups. In addition, luminescent cyanine and related dyes can be attached to fragments of DNA or RNA. The labeled fragments of DNA or RNA can be used as fluorescent hybridization probes to identify the presence and quantity of specific complementary nucleotide sequences in samples containing DNA or RNA. Also, the dye can be attached to a hormone or ligand (such as a hormone, protein, peptide, lymphokine, metabolite) which in turn can be attached to a receptor.

REACTIVE CYANINE DYES ARE DESCRIBED IN PATENTS FOR OTHER USES

Miraha et al. (U.S. Pat. No. 4,337,063), and Masuda et al. (U.S. Pat. Nos. 4,404,289; 4,405,711; have synthesized a variety of cyanine dyes possessing N-hydroxysuccinimide active ester groups. These patents show that these reagents can be used as photographic sensitizers. The possible fluorescence properties of these reagents are not mentioned in the patents and, indeed, fluorescence is not required for their process. Most of the dyes mentioned in these patents are only weakly fluorescent, they are not especially photostable, and their solubility properties are not optimal for many uses that would involve fluorescence detection of labeled materials.

Exekiel et al. (British Patent 1,529,202) have presented numerous cyanine dye derivatives that can be used as covalently reacting molecules. The reactive group used in these reagents are azine groups to which the mono and dichloro-triazine groups belong. The British patent relates to the developement and use of these reagents as photographic film sensitizers. Fluorescence is not required for the process and most of the reagents described are not fluorescent. The British patent does not relate to the development and use of reactive cyanine dyes for the purpose of detecting and quantifying labeled materials.

DESCRIPTION OF EMBODIMENTS

The present invention pertains to methods for covalently attaching luminescent cyanine and cyanine-type dyes to biological materials, non-biological molecules and macromolecules, and particles in order to make the material that has been labeled luminescent so that the labeled material can be detected and/or quantified by luminescence detection methods.

This invention relates to a method for the detection of a component in a liquid comprising adding to said liquid a dye selected from the group consisting of cyanine, merocyanine and styryl dyes which is soluble in the liquid and contains a substitutent to make it covalently reactive with amine and hydroxy groups, and possibly to aldehyde and sulfydryl groups, on said component so that it labels said component. The labeled component is then detected and/or quantified by luminescence or light absorption methods. If the labeled component is an antibody, DNA fragment, hormone, lymphokine, or drug, the labeled component can be used to identify the presence of a second component to which it binds, and then the second component can be detected and/or quantified.

Any available luminescence or light absorbing detecting step can be employed. For example, the detecting step can be an optical detecting step wherein the liquid is illuminated with light of first defined wavelengths. Light at second defined wavelengths that is fluoresced or phosphoresced by the labeled component is then detected. The detection also can be by optical light absorption. For example, the detecting step can comprise passing light of first defined wavelengths through the liquid and then ascertaining the wavelength of the light that is transmitted by the liquid.

If desired, the detecting step can comprise chemical analysis to chemically detect attachment of the cyanine or related chromophore to the component. The basic structures of cyanine, merocyanine and styryl dyes that can be modified to create covalent labeling reagents are shown below.

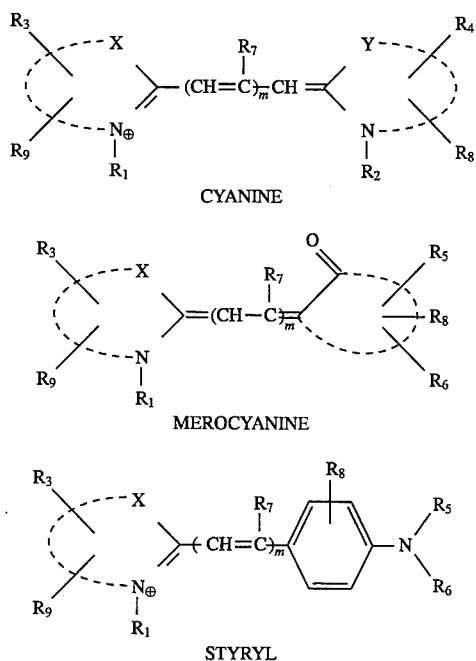

The following are more specific examples of polymethine cyanine type dyes:

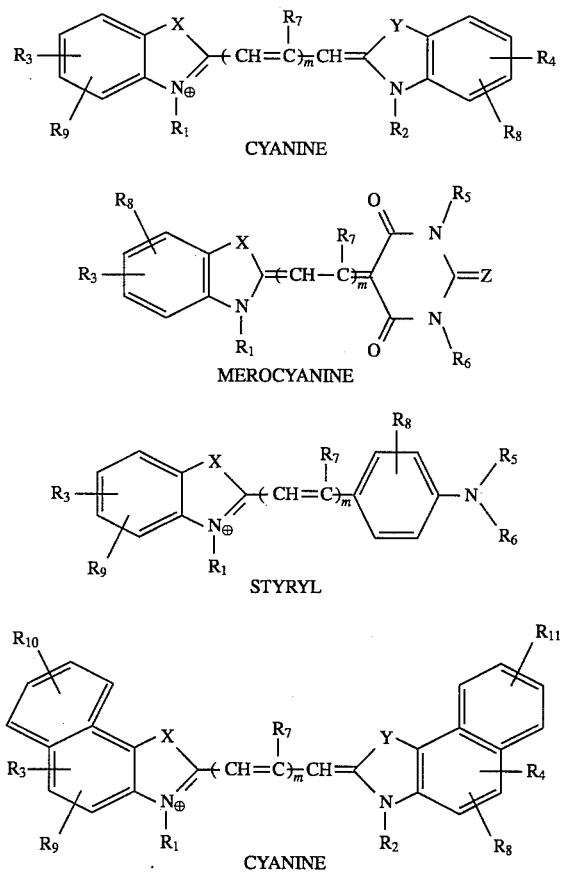

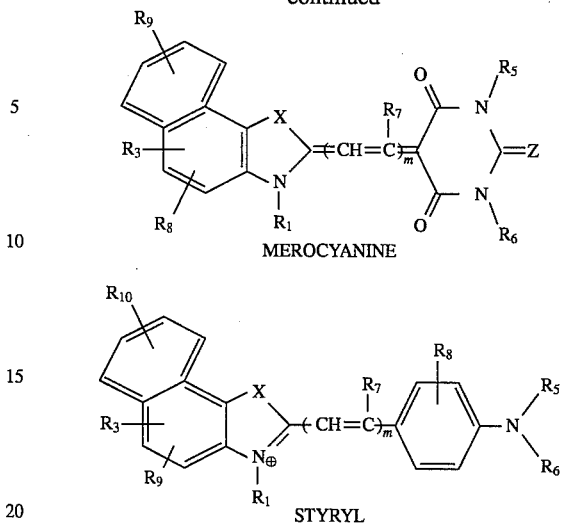

In these structures

X and Y are selected from the group consisting of O, S and

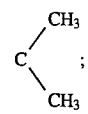

Z is selected from the group consisting of O and S; and m is an integer selected from the group consisting of 1, 2, 3 and 4.

In the above formulas, the number of methine groups determines in part the excitation color. The cyclic azine structures can also determine in part the excitation color. Often, higher values of m contribute to increased luminescence and absorbance. At values of m above 4, the compound becomes unstable. Thereupon, further luminescence can be imparted by modifications at the ring structures. When m=2, the excitation wavelength is about 650 nm and the compound is very fluorescent. Maximum emission wavelengths are generally 15–100 nm greater than maximum excitation wavelengths.

At least one, preferably only one, and possibly two or more of said $R_1$, $R_2$, $R_3$, $R_4$, $R_5$, $R_6$ and $R_7$ groups in each molecule is a reactive group for attaching the dye to the labeled component. For certain reagents, at least one of said $R_1$, $R_2$, $R_3$, $R_4$, $R_5$, $R_6$ and $R_7$ groups on each molecule may also be a group that increases the solubility of the chromophore, or affects the selectivity of labeling of the labeled component or affects the position of labeling of the labeled component by the dye.

In said formulas, at least one of said $R_8$, $R_9$ (if any) and $R_{10}$ (if any) groups comprises at least one sulfonate group. The term sulfonate is meant to include sulfonic acid because the sulfonate group is merely ionized sulfonic acid.

Reactive groups that may be attached directly or indirectly to the chromophore to form $R_1$, $R_2$, $R_3$, $R_4$, $R_5$, $R_6$ and $R_7$ groups may include reactive moieties such as groups containing isothiocyanate, isocyanate, monochlorotriazine, dichlorotriazine, mono- or di-halogen substituted pyridine, mono- or di-halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)- proprionamide, glyoxal and aldehyde.

Specific examples of $R_1, R_2, R_3, R_4, R_5, R_6$ and $R_7$ groups that are especially useful for labeling components with available amino-, hydroxy-, and sulfhydryl groups include:

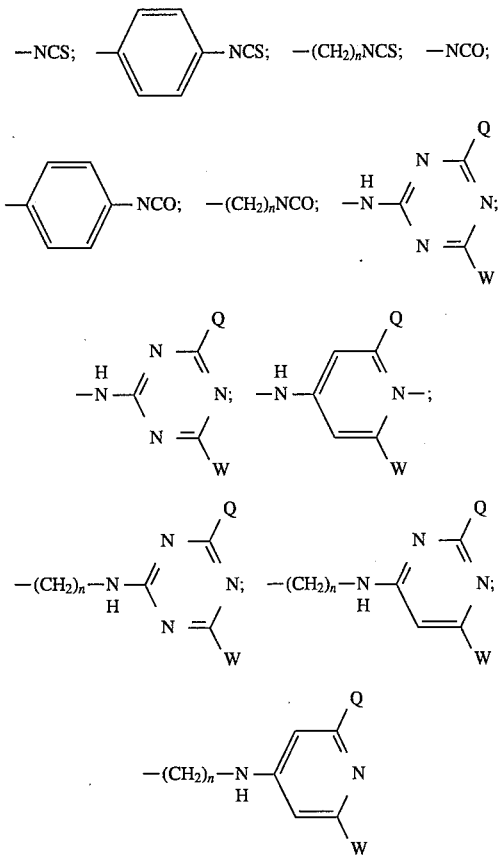

where at least one of Q or W is a leaving group such as I, Br,

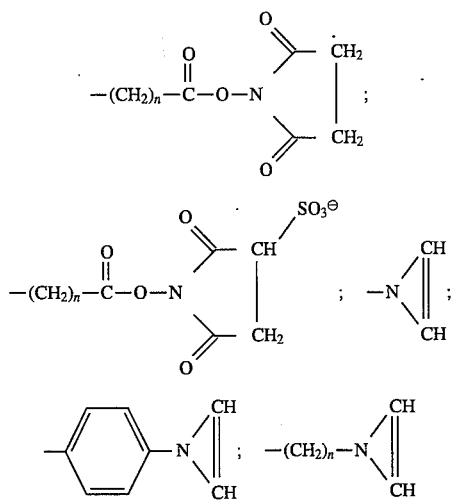

Specific examples of $R_1, R_2, R_3, R_4, R_5, R_6$ and $R_7$ groups that are especially useful for labeling components with available sulfhydryls which can be used for labeling antibodies in a two-step process:

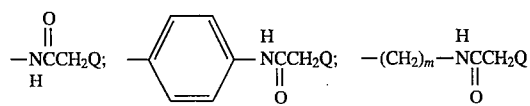

where Q is a leaving group such as I or Br,

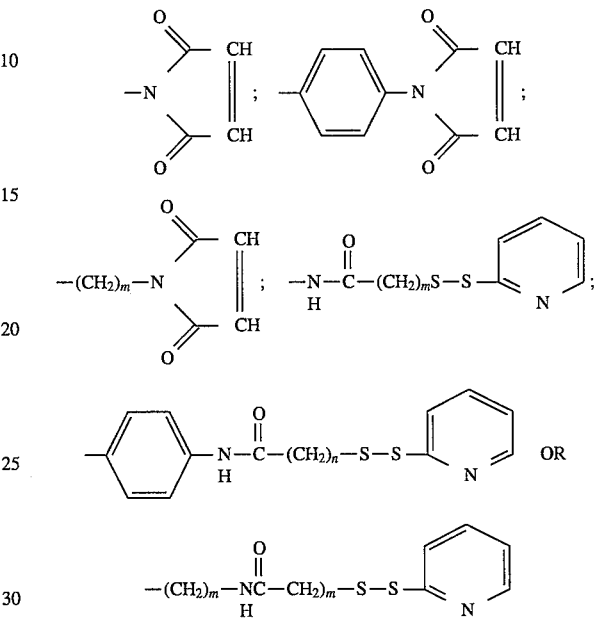

where n is 0 or an integer.

Specific examples of $R_1, R_2, R_3, R_4, R_5, R_6$ and $R_7$ groups that are especially useful for labeling components by light-activated cross linking include:

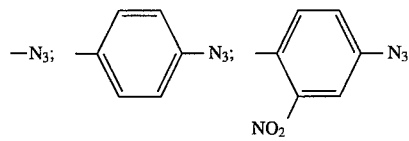

For the purpose of increasing water solubility or reducing unwanted nonspecific binding of the labeled component to inappropriate components in the sample or to reduce the interactions between two or more reactive chromophores on the labeled component which might lead to quenching of fluorescence, the $R_1, R_2, R_3, R_4, R_5, R_6$ and $R_7$ groups can be selected from the well known polar and electrically charged chemical groups. Examples are —E—F where F is hydroxy, sulfonate, sulfate, carboxylate, substituted amino or quaternary amino and where E is a spacer group such as —$(CH_2)_n$— where n is 0, 1, 2, 3 or 4. Useful examples include alkyl sulfonate; —$(CH_2)_3$ $SO^\ominus$; and —$(CH_2)_4$—$SO^{3\ominus}$.

The polymethine chain of the luminescent dyes of this invention may also contain one or more cyclic chemical groups that form bridges between two or more of the carbon atoms of the polymethine chain. These bridges might serve to increase the chemical or photo-stability of the dye and might be used to alter the absorption and emission wavelength of the dye or change its extinction coefficient or quantum yield. Improved solubility properties may be obtained by this modification.

In accordance with this invention the labeled component can be antibodies, proteins, peptides, enzyme substrates, hormones, lymphokines, metaboliltes, receptors, antigens, haptens, lectins, avidin, streptavidin, toxins, carbohydrates, oligosaccharides, polysaccharides, nucleic acids, deoxy nucleic acids, derivatized nucleic acids, derivatized deoxy nucleic acids, DNA fragments, RNA fragments, derivatized DNA fragments, derivatized RNA fragments, natural drugs, virus particles, bacterial particles, virus components, yeast components, blood cells, blood cell components, biological cells, noncellular blood components, bacteria, bacterial components, natural and synthetic lipid vesicles, synthetic drugs, poisons, environmental pollutants, polymers, polymer particles, glass particles, glass surfaces, plastic particles, plastic surfaces, polymer membranes, conductors and semiconductors.

A cyanine or related chromophore can be prepared which when reacted with a component can absorb light at 633 nm and the detecting step can employ a helium neon laser that emits light at this wavelength of the spectrum. Also, a cyanine or related dye can be prepared which when reacted with a component can absorb light maximally between 700 nm and 900 nm and the detecting step can employ a laser diode that emits light in this region of the spectrum.

SELECTIVITY

The reactive groups listed above are relatively specific for labeling particular functional groups on proteins and other biological or non-biological molecules, macromolecules, surfaces or particles provided that appropriate reaction conditions are used, including appropriate pH conditions.

PROPERTIES OF THE REACTIVE CYANINE, MEROCYANINE AND STYRYL DYES AND THEIR PRODUCTS

The spectral properties of the dyes of this invention are not appreciably altered by the functionalization described in this specification. The spectral properties of labeled proteins and other compounds are also not very different from the basic dye molecule that has not been conjugated to a protein or other material. The dyes described in this invention alone or conjugated to a labeled material generally have large extinction coefficients ($\epsilon$=100,000 to 250,000), have quantum yields as high as 0.4 in certain cases, and absorb and emit light in the spectral range of 400 to 900 nm. Thus, they are especially valuable as labeling reagents for luminescence detection.

OPTICAL DETECTION METHODS

Any method can be employed for detecting a labeled or stained component. The detecting method can employ a light source that illuminates the mixture containing the labeled material with light of first defined wavelengths. Known devices are employed that detect light at second wavelengths that is transmitted by the mixture or is fluoresced or luminesced by the mixture. Such detection devices include fluorescence spectrometers, absorption spectrophotometers, fluorescence microscopes, transmission light microscopes and flow cytometers, fiber optic sensors, and immunoassay instruments.

The method of this invention can also employ chemical analysis methods to detect attachment of the dye to the labeled component or components. Chemical analysis methods can include infrared spectrometry, NMR spectrometry, absorption spectrometry, fluorescence spectrometry, mass spectrometry and chromatographic methods.

EXAMPLE 1

Effect Of pH On The Conjugation Of Sulfoindodicarbocyanine With Protein

Samples of sheep gamma-globulin (4 mg/ml) in 0.1M carbonate buffers (pH 8.5, 8.9 and 9.4) were mixed at room temperature with a 10 fold molar excess of the following sulfoindodicarbo-cyanine active-ester (m=2).

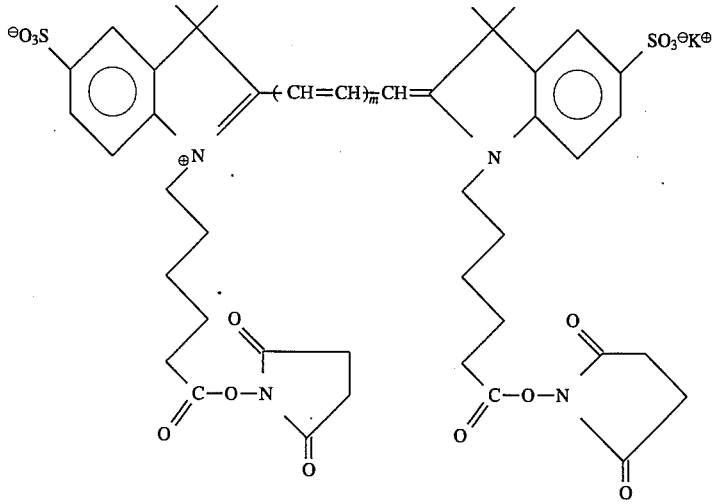

At appropriate times, ranging from 5 seconds to 30 minutes, protein samples were separated from non-covalently attached dye by gel permeation chromatography on Sephadex® G-50. Maximum labeling of the protein occurred after 10 minutes, yielding final dye/protein mole ratios of 5.8, 6.4 and 8.2 for the samples incubated at pH 8.5, 8.9 and 9.4, respectively. The times required to produce a dye/protein ratio of 5 and the quantum yields of the products at the different pH levels are shown in the table below:

| pH | time (sec.) | OY |
|---|---|---|
| 8.5 | 115 | 0.09 |
| 8.9 | 53 | 0.09 |
| 9.4 | 6.5 | 0.17 |

These data indicate that protein labeling with this dye is better at pH 9.4 than below 9. In the higher pH buffer the conjugation reaction was very rapid, but the labeling efficiency was excellent and the product was more fluorescent. The quantum yield value represents the average quantum yield per dye molecule on the labeled protein.

EXAMPLE 2

Sulfoindocarbocyanine Active Ester Conjugation With Protein

Sheep gamma-globulin (1 mg/ml) dissolved in pH 7.4 phosphate buffered saline (PBS) was adjusted to pH 9.4 using 0.1 M sodium carbonate. Cyanine dye labeling agent (structure in Example 1, m=1) was added to aliquots of this protein solution to give various mole ratios of dye/protein. After 30 minutes incubation at room temperature the mixtures were separated by Sephadex® G-50 gel permeation chromatography eluting with PBS. The mole ratio of dyes covalently attached to the proteins in the products were 1.2, 3.5, 5.4, 6.7 and 11.2 for initial dye/protein ratios of 3, 6, 12, 24 and 30, respectively.

EXAMPLE 3

Labeling AECM-Dextran With A Sulfoindodicarbocyanine

N-Aminoethyl-carboxamidomethyl (AECM) dextran containing an average of 16 amino groups per dextran molecule was synthesized from dextran, average MW 70000 (Inman, J. K., J. Immunol. 114:704–709 [1975]). A portion of the AECM-dextran (1 mg/250 µl) dissolved in 0.1 M carbonate buffer, pH 9.4 was added to 0.2 mg of the sulfoindodicarbocyanine active ester (structure in Example 1, m=2) giving a dye/protein mole ratio of 10. The mixture was stirred for 30 minutes at room temperature. The dextran was then separated from nonconjugated dye by Sephadex® G-50 gel permeation chromatography using ammonium acetate (50 mM) as elution buffer. An average of 2.2 dye molecules were covalently linked to each dextran molecule.

EXAMPLE 4

Sulfoindodicarbocyanine Active Ester Labeling of Specific Antibody

Sheep gamma-globulin specific against murine lgG (1 mg/ml) in 0.1M carbonate buffer (pH 9.4) was mixed with sulfoindodicarbocyanine active ester (structure in Example 1, m=2) at a ratio of 8 dye molecules/protein molecule. After incubating 30 minutes at room temperature, the labeling mixture was separated by gel filtration over Sephadex® G-50 equilibrated with phosphate buffered saline (pH 7.4). The recovered protein contained an average of 4.5 dye molecules covalently attached to each protein molecule.

EXAMPLE 5

Staining and Microscopic Visualization Of Human Lymphocytes With Sulfoindodicarbocyanine Dye Conjugated To Sheep Anti-mouse-lgG Antibody Freshly isolated peripheral blood lymphocytes were treated at 0° C. for 30 minutes with mouse anti-beta2-microglobulin (0.25 µg $10^6$ cells). The cells were washed twice with DMEM buffer and were then treated with the sulfoindodicarbocyanine-labeled sheep anti-mouse-lgG antibody (1 µg/$10^6$ cells). After a 30 minute incubation at 0° C., the excess antibody was removed by centrifuging the cells and the cells were again washed twice with DMEM buffer. Aliquots of the cells were fixed on slides for analysis by fluorescence microscopy. Under the microscope the lymphocytes on the slide were illuminated with light at 610–630 nm and the fluorescence at 650–700 nm was detected with a COHU red Sensitive intensified television camera attached to an image digitizer and television monitor. The cells stained by this method showed fluorescence under the microscope. In a control experiment, use of the primary mouse anti-beta2-microglobulin antibody was omitted but the staining and analysis was otherwise carried out as described above. The control sample showed no fluorescence under the microscope indicating that the sulfoindocyanine-labeled sheep anti-mouse antibody does not give significant nonspecific binding to lymphocytes.

I claim:

1. A method for labeling a component of an aqueous liquid comprising:

(a) adding to a liquid which contains a component selected from the group consisting of proteins, sugars, cells, nucleic acids and combinations thereof, a luminescent dye selected from the group consisting of cyanine, merocyanine and styryl dyes having the structures

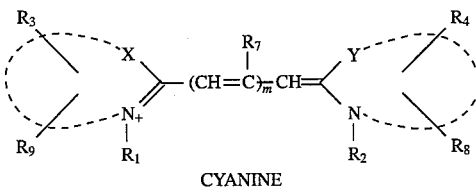

CYANINE

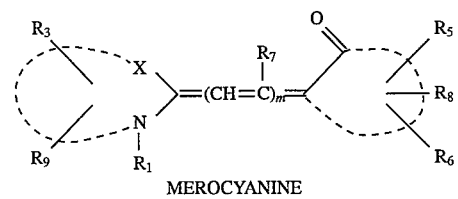

MEROCYANINE

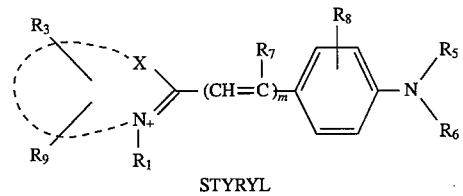

STYRYL wherein:
the dotted lines each represent carbon atoms necessary for the formulation of said cyanine, merocyanine and styryl dyes;
X and Y are selected from the group consisting of O, S, and $CH_3$—C—$CH_3$;

m is an integer selected from the group consisting of 1, 2, 3 and 4;

at least one of said $R_1, R_2, R_3, R_4, R_5, R_6$ and $R_7$ groups contains a reactive group to make said dye covalently reactive with an amine, aldehyde, sulfhydryl or hydroxy group on said component; and, at least one of said $R_8$ and $R_9$ groups comprises a sulfonic acid or sulfonate group attached to an aromatic nucleus of said dye; and (b) reacting said dye with said component so that said dye covalently binds to and labels said component.

2. The method of claim 1 wherein said dye contains more than one sulfonic acid or sulfonate group.

3. The method of claim 1 wherein said dye is a cyanine dye.

4. The method of claim 1 wherein said dye is a merocyanine dye.

5. The method of claim 1 wherein said dye is a styryl dye.

6. A method for labeling a first component and using the labeled first component to bind with a second component to form a labeled second component, said method comprising:

(a) adding to an aqueous liquid containing a first component selected from the group consisting of antibodies, antigens and nucleic acids, a luminescent dye selected from the group consisting of cyanine, merocyanine and styryl dyes having the structures:

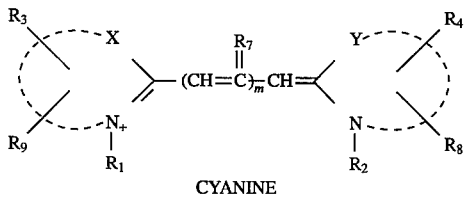
CYANINE

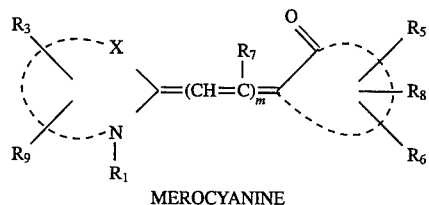
MEROCYANINE

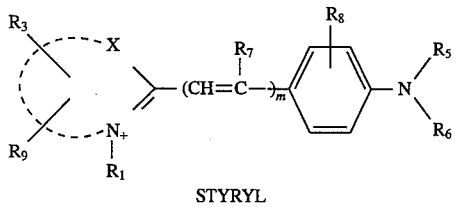
STYRYL wherein:
the dotted lines each represent carbon atoms necessary for the formulation of one ring to three fused rings having 5 to 6 carbon atoms in each ring;

X and Y are selected from the group consisting of O, S, and $CH_3$—C—$CH_3$;

m is an integer selected from the group consisting of 1, 2, 3 and 4;

at least one of said $R_1, R_2, R_3, R_4, R_5, R_6$ and $R_7$ groups contains at least one reactive group to make said dye covalently reactive with said first component and, at least one of said $R_8$ and $R_9$ groups comprises a sulfonic acid or sulfonate group attached to an aromatic nucleus of said dye;

(b) reacting said dye with said first component so that said dye covalently binds to and luminescently labels said first component to provide a labeled first component;

(c) treating a sample with said labeled first component for binding said labeled first component to a second component, if any, present in said sample, said second component having at least a portion comprised of an antigen, antibody or complementary nucleic acid capable of binding to said respective antibody, antigen or nucleic acid of said labeled first component to form a labeled second component; and (d) detecting said labeled second component by an optical method.

7. The method of claim 6 wherein said dye contains more than one sulfonic acid or sulfonate group.

8. The method of claim 6 wherein said dye reacts with an amine, hydroxy or sulfhydryl group on said first component.

9. The method of claim 6 wherein said dye reacts with an aldehyde group on said first component.

10. The method of claim 6 wherein said dye is a cyanine dye and reacts with an amine or hydroxy group on said first component.

11. The method of claim 6 wherein said dye is a cyanine dye and reacts with an aldehyde or sulfhydryl group on said first component.

12. The method recited in claim 6 wherein said reactive group is selected from the group consisting of isothiocyanate, isocyanate, monochlorotriazine, dichlorotriazine, mono- or di-halogen substituted pyridine, mono- or di-halogen substituted diazine, maleimide, aziridine, sulfonyl halide, acid halide, hydroxysuccinimide ester, hydroxysulfosuccinimide ester, imido ester, hydrazine, azidonitrophenyl, azide, 3-(2-pyridyl dithio)-proprionamide, glyoxal and aldehyde.

13. A method for labeling a component of an aqueous liquid comprising:

(a) adding to a liquid which contains a component selected from the group consisting of proteins, sugars, cells, nucleic acids and combinations thereof, a luminescent dye covalently reactive with an amine, aldehyde, sulfhydryl or hydroxy group on said component and at least one sulfonic acid or sulfonate group attached to an aromatic nucleus of said dye; wherein said dye is selected from the group consisting of:

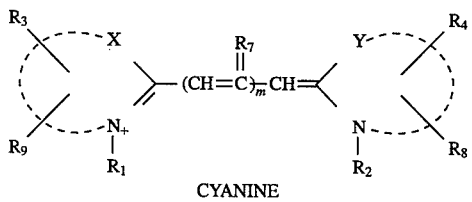
CYANINE

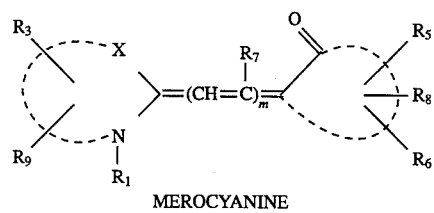
MEROCYANINE

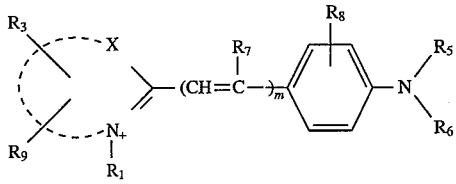

STYRYL wherein:
the dotted lines each represent carbon atoms necessary for the formulation of one ring to three fused rings having 5 to 6 carbon atoms in each ring; X and Y are selected from the group consisting of O, S,

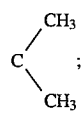

m is an integer selected from the group consisting of 1, 2, 3 and 4;

at least one of said $R_1$, $R_2$, $R_3$, $R_4$, $R_5$, $R_6$ and $R_7$ groups contains at least one moiety selected from the group consisting of isothiocyanate, isocyanate, monochlorotriazine, dichlorotriazine, mono- or di-halogen substituted pyridine, mono or di-halogen substituted diazine, maleimide, aziridine, azidonitrophenyl, azide, 3-(2-pyridyl dithio)-proprionamide, glyoxal and aldehyde; and at least one of said $R_8$ and $R_9$ groups comprises at least one arylsulfonyl or arylsulfonate moiety; and (b) reacting said dye with said component so that said dye covalently binds to and labels said component.

14. The method of claim 13 wherein said at least one $R_1$, $R_2$, $R_3$, $R_4$, $R_5$, $R_6$ and $R_7$ groups contains at least one moiety selected from the group consisting of:

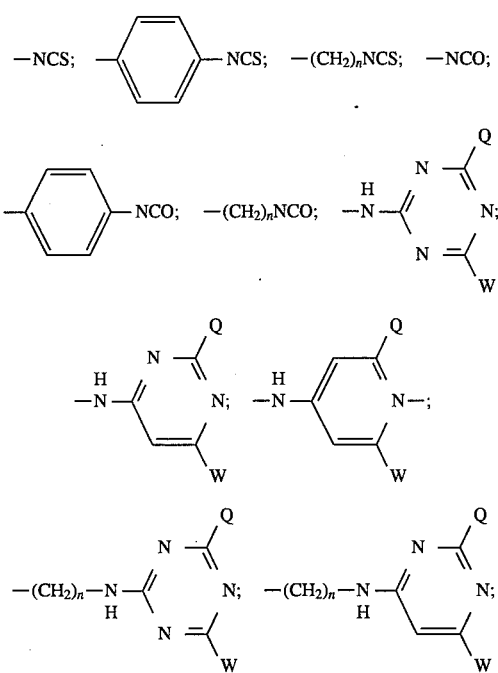

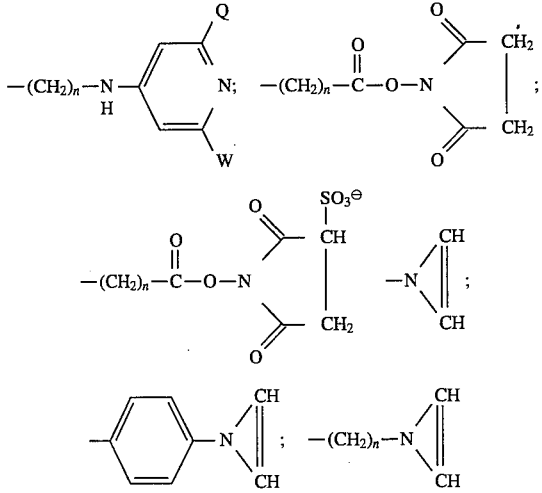

where at least one of Q or W is selected from the group consisting of Cl; Br; I; and n is zero or any integer.

15. The method of claim 13 wherein at least one of said $R_1$, $R_2$, $R_3$, $R_4$, $R_5$, $R_6$ and $R_7$ groups contains at least one moiety selected from the group consisting of:

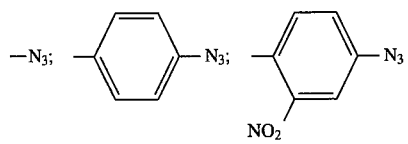

16. The method of claim 13 wherein at least one of said $R_1$, $R_2$, $R_3$, $R_4$, $R_5$, $R_6$ and $R_7$ groups also contains at least one moiety selected from the group consisting of hydroxy, sulfonate, sulfate, carboxylate and substituted amine or quaternary amine groups.

17. The method of claim 13 including the step of optically detecting said labeled component.

18. The method of claim 17 wherein said detecting step comprises illuminating said labeled component with light and then detecting light that is fluoresced by said labeled component.

19. The method of claim 17 wherein said detecting step includes light excitation with a laser.

20. The method of claim 17 wherein said detecting step employs fluorescence microscopy.

21. The method of claim 17 wherein said detecting step employs flow cytometry.

22. The method of claim 17 wherein said detected component is quantified.

23. A method comprising:

(a) in a liquid which contains a first component, at least a portion of said first component being selected from the group consisting of proteins, sugars, nucleic acids, cells and combinations thereof, and having an amino, hydroxy or sulfhydryl nucleophile, labeling said first component with a water soluble luminescent dye comprising a cyanine having the structure

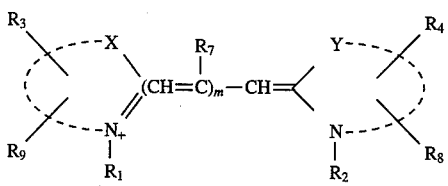

wherein: the dotted lines each represent carbon atoms necessary for the formation of said dye;

X and Y are each selected from the group consisting of O, S and $CH_3$—C—$CH_3$;

m is an integer selected from the group consisting of 1, 2 and 3;

at least one of said $R_1$, $R_2$, $R_3$, $R_4$, and $R_7$ group reacts with amino, hydroxy or sulfhydryl nucleophiles of said first component and is a reactive moiety selected from a group containing

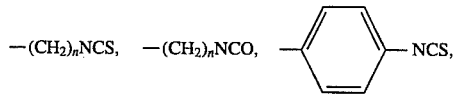

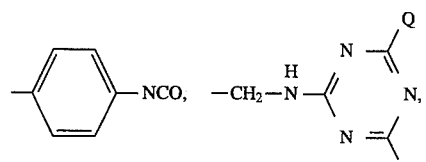

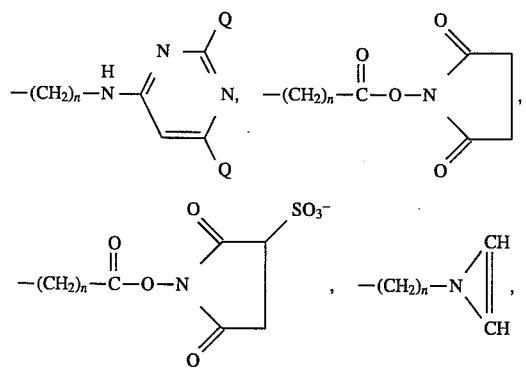

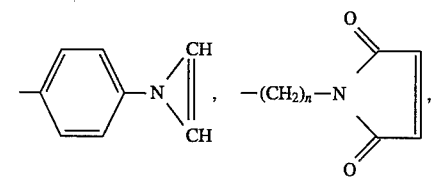

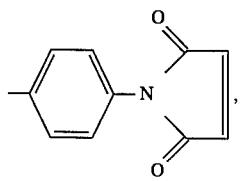

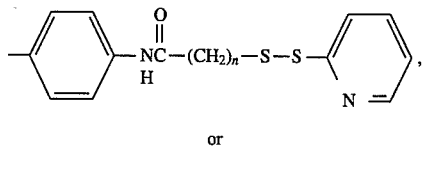

or

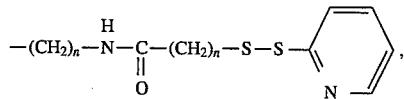

wherein Q is Br or Cl, and n=0, 1, 2, 3, 4, 5, 6, 7 or 8 for $R_3$, $R_4$, and $R_7$, and n=1, 2, 3, 4, 5, 6, 7 or 8 for $R_1$ and $R_2$;

and when any one of said $R_3$, $R_4$, and $R_7$ groups is not selected from one said reactive moiety, said remaining $R_3$, $R_4$, and $R_7$ are hydrogen or E-F, a polar group wherein E is a spacer group having the structure —$(CH_2)_n$— and n of said spacer group= 0, 1, 2, 3, or 4, and F is hydroxy, sulfonate, sulfate, carboxylate, or a lower alkyl substituted amino;

and when any one of said $R_1$ and $R_2$ groups is not selected from one said reactive moiety, said remaining $R_1$ and $R_2$ are a lower alkyl or said E-F and n of said spacer group=1, 2, 3, or 4;

at least one said $R_8$ and $R_9$ groups is selected from the group consisting of an arylsulfonic acid and an arylsulfonate moiety for conferring improved luminescence to said dye when in use as compared to a dye which does not have said at least one arylsulfonic acid or arylsulfonate moiety;

and when one of said $R_8$ or $R_9$ group is not an arylsulfonic acid or an arylsulfonate, said remaining $R_8$ or $R_9$ group is a hydrogen;

(b) contacting said labeled first component with a second component having at least a portion thereof capable of binding to said first component to form a labeled second component; and, (c) detecting the presence of said labeled first and second components by optical methods.

\* \* \* \* \*

UNITED STATES PATENT AND TRADEMARK OFFICE
CERTIFICATE OF CORRECTION

PATENT NO. : 5,569,587
DATED : October 29, 1996
INVENTOR(S) : Waggoner

It is certified that error appears in the above-identified patent and that said Letters Patent is hereby corrected as shown below:

Column 2,
Line 39, delete "6r" and substitute therefor -- or --;

Column 4,
Line 56, delete "86%" and substitute therefor -- 80% --;

Column 7,
Line 52, delete "Were" and substitute therefor -- were --;

Column 8,
Lines 5 and 51, delete "sulfobytyl" and substitute therefor -- sulfobutyl --;

Column 15,
Line 42, after "Br," insert -- Cl, --;

Column 16,
Line 54, delete each occurrence of "SO⁻" and substitute therefor -- $SO^{3-}$ --;

Column 19,
Line 2 (in the table), delete "OY" and substitute therefor -- QY --;

Column 21,
Line 55, after "of" delete "one ring to three fused rings having 5 to 6 carbon atoms in each ring" and substitute therefor -- said cyanine, merocyanine and styryl dyes --;

UNITED STATES PATENT AND TRADEMARK OFFICE
CERTIFICATE OF CORRECTION

PATENT NO.   : 5,569,587
DATED        : October 29, 1996
INVENTOR(S)  : Waggoner It is certified that error appears in the above-identified patent and that said Letters Patent is hereby corrected as shown below:

Column 23,
Line 13, after "of" delete "one ring to three fused rings having 5 to 6 carbon atoms in each ring" and substitute therefor -- said cyanine, merocyanine and styryl dyes --;

Column 26,
Line 42, delete "R" and substitute therefor -- $R_8$ --.

Signed and Sealed this

Twenty-seventh Day of November, 2001

Attest:

*Nicholas P. Godici*

NICHOLAS P. GODICI
*Attesting Officer*  *Acting Director of the United States Patent and Trademark Office*